(12) United States Patent
Cheng et al.

(10) Patent No.: US 7,815,927 B2
(45) Date of Patent: Oct. 19, 2010

(54) TERPOLYMERS FOR CONTROLLED RELEASE OF BIOACTIVE AGENTS FROM IMPLANTABLE MEDICAL DEVICES

(75) Inventors: Peiwen Cheng, Santa Rosa, CA (US); Kishore Udipi, Santa Rosa, CA (US); Mingfei Chen, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 381 days.

(21) Appl. No.: 11/683,836

(22) Filed: Mar. 8, 2007

(65) Prior Publication Data
US 2008/0220046 A1   Sep. 11, 2008

(51) Int. Cl.
*A61L 27/00* (2006.01)
*A61F 2/00* (2006.01)
*A61K 31/56* (2006.01)
*A61K 31/7105* (2006.01)
*A61K 33/00* (2006.01)
*A61K 39/395* (2006.01)

(52) U.S. Cl. .............. 424/426; 424/130.1; 424/718; 427/2.24; 514/169; 514/44; 623/1.1

(58) Field of Classification Search .............. None
See application file for complete search history.

(56) References Cited

U.S. PATENT DOCUMENTS

| 5,362,718 A | 11/1994 | Skotnicki et al. |
| 6,015,815 A | 1/2000 | Mollison |
| 6,329,386 B1 | 12/2001 | Mollison |
| 2005/0084515 A1* | 4/2005 | Udipi et al. .............. 424/426 |
| 2006/0195142 A1* | 8/2006 | Shalaby .............. 606/228 |

FOREIGN PATENT DOCUMENTS

WO    WO2004/014447    2/2004

\* cited by examiner

*Primary Examiner*—Andrew D Kosar
*Assistant Examiner*—Sarah Al-Awadi

(57) ABSTRACT

Disclosed herein are implantable medical devices comprising controlled release terpolymers and at least one drug releasable from said terpolymers coating. The terpolymers of the present invention are comprised of acrylate and/or vinyl monomers.

1 Claim, 2 Drawing Sheets

TERPOLYMERS FOR CONTROLLED RELEASE OF BIOACTIVE AGENTS FROM IMPLANTABLE MEDICAL DEVICES

FIELD OF THE INVENTION

The present invention relates to implantable medical devices having terpolymer controlled release coatings.

BACKGROUND OF THE INVENTION

Recently, highly biocompatible polymers have been formulated to provide implantable medical devices with coatings. These coatings not only increase an implant's tissue compatibility but can also function as bioactive agent reservoirs. However, designing polymer coatings for medical devices has proven problematic. Medical device coatings must be non-toxic, durable and adhere well to device surfaces. Additionally, when the medical device comes into intimate contact with tissues such as blood and internal organs it must also be biocompatible. Furthermore, if the medical device is designed to be pliable either in operation or deployment, the coating must resist cracking, fracture and delamination.

Moreover, polymer coatings on medical devices intended to act as bioactive agent (drug) eluting devices must not only be biocompatible, structurally stable, resistant to delamination, but also chemically compatible with the drug to be administered. Furthermore, if the coating is also intended to control the drug's release rate into adjacent tissue the polymer used must possess other highly specialized properties as well such as, but not limited to appropriate glass transition temperatures and appropriate hydrophilicity/hydrophobicity indexes.

One of the most widely used techniques to modify the properties of a polymer material is to blend different polymers or copolymers together into a single mixture. The resulting polymer mixtures possess a combination of properties of each polymer or copolymer component of the blend. Not all polymers, however, are miscible and thus instead of forming a uniform blend, the polymers can form immiscible mixtures subject to phase separation and delamination. When used as coatings for medical devices this problem becomes even more pronounced. One polymer component may have a stronger affinity for the medical device surface than another and thus may layer closer to the medical device surface. The polymer component having less affinity and avidity for the medical device surface migrates away from the medical device surface resulting in a bi-layer where each polymer component retains its individual properties and the coating no longer functions as a cohesive uniform substance. When bioactive agents are included in the mixture, the problems associated with immiscibility are magnified by the addition of yet a third chemical species having unique chemical properties. An additional variable is introduced by the material of the medical device substrate.

Thus, prior art methods used to develop polymer coatings, specifically drug-eluting coatings, have been largely by trial and error. Recently, the present inventors have developed methods for reducing uncertainty in coating design by matching polymer components with bioactive agents based, in part, on solubility factors.

Thus, there is a need for improved polymeric materials suitable for coating implantable medical devices. Therefore, it is an object of the present invention to provide compositions and associated methods for a wide range of biocompatible terpolymers, useful for coating implantable medical devices.

SUMMARY OF THE INVENTION

The present invention pertains to controlled release polymers suitable for coating medical device. More specifically, the present invention refers to controlled release terpolymers suitable for coating implantable medical devices. The terpolymers of the present invention can be fine tuned to release drugs at various rates.

In one embodiment of the present invention, an implantable medical device is provided comprising a controlled-release terpolymer coating on at least one surface of the medical device and at least one drug, the drug releasable from the terpolymer coating.

In another embodiment of the present invention, the terpolymer comprises three monomers selected from the group comprising acrylate monomers and vinyl monomers. In another embodiment, the terpolymer comprises at least one acrylate monomer. In yet another embodiment, the terpolymer comprises at least one vinyl monomer. In another embodiment, the acrylate monomer is selected from the group consisting of methyl methacrylate, ethyl methacrylate, butyl methacrylate, hexyl methacrylate, 2-(ethoxy ethylmethacrylate), methyl acrylate, ethyl acrylate, hexyl acrylate, and butyl acrylate, hydroxyl ethylmethacrylate, hydroxyl propylmethacrylate. In another embodiment, the vinyl monomer is N-vinyl pyrrolidinone or vinyl acetate.

In another embodiment of the present invention, controlled release terpolymer comprises the structure of Formula 3,

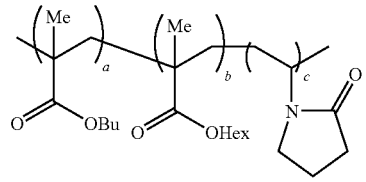

Formula 3

Bu = CH$_2$CH$_2$CH$_2$CH$_3$
Hex = CH$_2$CH$_2$CH$_2$CH$_2$CH$_2$CH$_3$

Bu=CH$_2$CH$_2$CH$_2$CH$_3$

Hex=CH$_2$CH$_2$CH$_2$CH$_2$CH$_2$CH$_3$ wherein a is an integer from about 2 to about 30,000, b is an integer from about 2 to about 30,000, and c is an integer from about 2 to about 30,000. In another embodiment, a is an integer from about 2 to about 15,000, b is an integer from about 2 to about 15,000, and c is an integer from about 2 to about 15,000.

In another embodiment, the at least one drug is selected from the group consisting of FKBP-12 binding agents, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. In another embodiment, the drug comprises at least one compound selected from the group consisting of sirolimus (rapamycin), tacrolimus (FK506), everolimus (certican), temsirolimus (CCI-779) and zotarolimus (ABT-578). In another embodiment, the drug comprises zotarolimus.

In another embodiment of the present invention, the medical device is selected from the group consisting of vascular stents, stent grafts, urethral stents, bile duct stents, catheters, guide wires, pacemaker leads, bone screws, sutures and prosthetic heart valves.

DEFINITION OF TERMS

Figure 1:
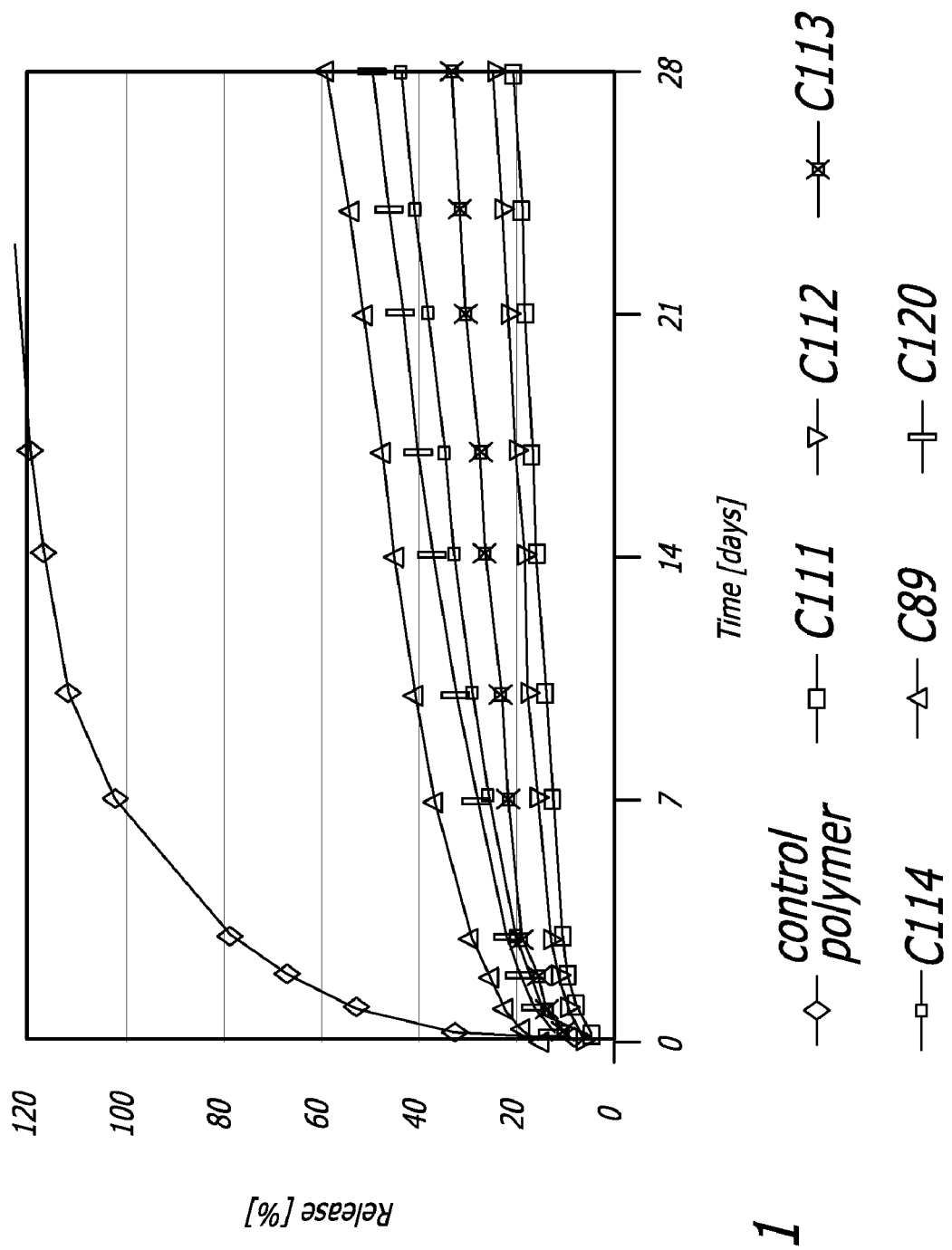
FIG. 1 depicts the drug elution profile of rapamycin from stents coated with terpolymers 1, 2, 3, 4, 5 and 10 (see Table 1) according to the teachings of the present invention.

Prior to setting forth the invention, it may be helpful to an understanding thereof to set forth definitions of certain terms that will be used hereinafter:

Backbone: As used here in "backbone" refers to the main chain of a polymer or copolymer of the present invention. As used herein the backbone comprises acrylate based chains.

Copolymer: As used herein, a "copolymer" is a macromolecule produced by the simultaneous or step-wise polymerization of two or more dissimilar units such as monomers. Copolymers include bipolymers (two dissimilar units), terpolymers (three dissimilar units), etc.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Drug(s): As used herein "drug" shall include any bioactive agent having a therapeutic effect in an animal. Exemplary, non limiting examples include anti-proliferatives including, but not limited to, macrolide antibiotics including FKBP 12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

Exemplary FKBP 12 binding compounds include sirolimus (rapamycin) (Formula 2), tacrolimus (FK506), everolimus (certican or RAD-001), temsirolimus (CCI-779 or amorphous rapamycin 42-ester with 3-hydroxy-2-(hydroxymethyl)-2-methylpropionic acid) and zotarolimus (ABT-578). Additionally, and other rapamycin hydroxyesters may be used in combination with the terpolymers of the present invention.

Ductility: As used herein "ductility, or ductile" is a polymer attribute characterized by the polymer's resistance to fracture or cracking when folded, stressed or strained at operating temperatures. When used in reference to the polymer coating compostions of the present invention the normal operating temperature for the coating will be between room temperature and body temperature or approximately between 15° C. and 40° C. Polymer durability in a defined environment is often a function of its elasticity/ductility.

Glass Transition Temperature (Tg): As used herein glass transition temperature (Tg) refers to a temperature wherein a polymer structurally transitions from a elastic pliable state to a rigid and brittle state.

Hydrophilic: As used herein in reference to the bioactive agent, the term "hydrophilic" refers to a bioactive agent that has a solubility in water of more than 200 micrograms per milliliter.

Hydrophobic: As used herein in reference to the bioactive agent the term "hydrophobic" refers to a bioactive agent that has a solubility in water of no more than 200 micrograms per milliliter.

Terpolymer: As used herein, "terpolymer" refers to a polymer synthesized from three different monomers.

$M_n$: As used herein $M_n$ refers to number-average molecular weight. Mathematically it is represented by the following formula:

$$M_n = \Sigma_i N_i M_i / \Sigma_i N_i, \text{ wherein the } N_i \text{ is the number of moles whose weight is } M_i.$$

$M_w$: As used herein $M_w$ refers to weight average molecular weight that is the average weight that a given polymer may have. Mathematically it is represented by the following formula:

$$M_w = \Sigma_i N_i M_i^2 / \Sigma_i N_i M_i, \text{ wherein } N_i \text{ is the number of molecules whose weight is } M_i.$$

DETAILED DESCRIPTION OF THE INVENTION

The present invention pertains to controlled release polymers suitable for coating medical devices. More specifically, the present invention refers to controlled release terpolymers suitable for coating implantable medical devices. The polymers of the present invention can be fine tuned to release drugs at various rates.

The terpolymers of the present invention form drug encapsulating matrices that enable the controlled release of drugs there from. More specifically the drug release, or eluting, rates are controlled by, amongst other properties, the glass transition temperature (Tg) of the polymer. The biocompatible controlled-release coatings described herein are resilient, that is they do not delaminate from the medical device or suffer damage rendering the coating defunct. The terpolymers of the present invention are biocompatible and stable, that is they do not biodegrade.

Medical devices suitable for coating with the controlled release terpolymers of the present invention include, but are not limited to, vascular stents, shunts, stent grafts, urethral stents, bile duct stents, catheters, guide wires, needles, pacemaker leads, pacemakers, defibrillators, bone screws, sutures and heart valves.

The controlled release terpolymers of the present invention comprise three monomers. In one embodiment of the present invention, the controlled drug releasing terpolymers comprise acrylic monomers. Additional monomers useful in the polymers of the present invention include vinyl-containing monomers such as, but are not limited to, N-vinyl pyrrolidone. By varying the ratio of monomers, as well as the reaction conditions, the properties of the polymers can be fine tuned for drug delivery, more specifically for the controlled release of various drugs. The terpolymers of the present invention are also suitable for the controlled-release of both hydrophobic and hydrophilic drugs, either independently or in combination.

In one embodiment of the present invention, a controlled drug releasing terpolymeric coating is provided for an implantable medical device comprising monomers including, but not limited to, acrylate monomers and vinyl-containing monomers. Acrylate monomers suitable for the synthesis of the terpolymers of the present invention include, but are not limited to, methyl methacrylate, hexyl methacrylate, butyl methacrylate, ethyl methacrylate, lauryl methacrylate, hydroxyl propylmethacrylate, 2-(ethoxy ethylmethacrylate), hydroxyl ethylmethacrylate, methyl methacrylate, 2-ethoxyethyl methacrylate, methyl acrylate, ethyl acrylate, hexyl acrylate, and butyl acrylate.

Vinyl monomers suitable for use in the synthesis of the terpolymers of the present invention include, but are not limited to, N-vinyl pyrrolidone and vinyl acetate.

In one embodiment of the present invention the controlled release terpolymer comprises butyl methacrylate (BMA), hexyl methacrylate (HMA), and N-vinyl pyrrolidone (NVP) as depicted in Formula 3.

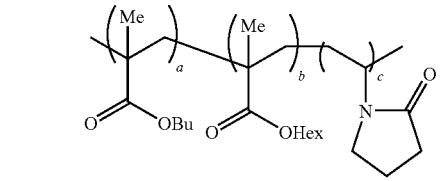

Formula 3

Bu = CH$_2$CH$_2$CH$_2$CH$_3$
Hex = CH$_2$CH$_2$CH$_2$CH$_2$CH$_2$CH$_3$

Bu=CH$_2$CH$_2$CH$_2$CH$_3$

Hex=CH$_2$CH$_2$CH$_2$CH$_2$CH$_2$CH$_3$

In one embodiment of the present invention, a is an integer from about 2 to about 30,000, b is an integer from about 2 to about 30,000, and c is an integer from about 2 to about 30,000. In additional embodiments, a is an integer ranging from 10 to 20,000; from 20 to 10,000; from 100 to 5,000; from 200 to 4,000; from 300 to 3,000; from 400 to 2,000; or from 500 to 1000. In additional embodiments, b is an integer ranging from 10 to 20,000; from 20 to 10,000; from 100 to 5,000; from 200 to 4,000; from 300 to 3,000; from 400 to 2,000; or from 500 to 1000. In additional embodiments, c is an integer ranging from 10 to 20,000; from 20 to 10,000; from 100 to 5,000; from 200 to 4,000; from 300 to 3,000; from 400 to 2,000; or from 500 to 1000.

In another embodiment of the present invention, the terpolymer coating is coated on an implantable medical device and further comprises a drug. In another embodiment, the polymer-coated medical device releases the drug with a drug elution profile including, but not limited to, a rapid large burst of drug followed by a steady release rate; a rapid small burst of drug followed by a steady release rate; and a gradual release of drug without a burst.

As discussed above, the physical properties of the terpolymers can be fine tuned so that the polymers can optimally perform for their intended use. Properties that can be fine tuned, without limitation, include Tg, molecular weight (both $M_n$ and $M_w$), polydispersity index (PDI, the quotient of $M_w/M_n$), degree of elasticity and degree of amphiphilicity. In another embodiment of the present invention, the Tg of the terpolymers range from about −10° C. to about 190° C. In another embodiment, the Tg of the terpolymers range from about −5° C. to about 180° C. In another embodiment, the Tg of the terpolymers range from about 0° C. to about 170° C. In another embodiment, the Tg of the terpolymers range from about 5° C. to about 160° C. In another embodiment, the Tg of the terpolymers range from about 10° C. to about 150° C. In another embodiment, the Tg of the terpolymers range from about 15° C. to about 140° C. In another embodiment, the Tg of the terpolymers range from about 20° C. to about 130° C. In another embodiment, the Tg of the terpolymers range from about 25° C. to about 120° C. In another embodiment, the Tg of the terpolymers range from about 30° C. to about 110° C. In another embodiment, the Tg of the terpolymers range from about 35° C. to about 100° C. In another embodiment, the Tg of the terpolymers range from about 40° C. to about 90° C. In another embodiment, the Tg of the terpolymers range from about 45° C. to about 80° C. In another embodiment, the Tg of the terpolymers range from about 50° C. to about 70° C. In another embodiment, the Tg of the terpolymers range from about 55° C. to about 60° C. In still another embodiment of the present invention, the PDI of the terpolymers range from about 1.3 to about 4. In another embodiment, the PDI of the terpolymers range from about 1.5 to about 3.5. In another embodiment, the PDI of the terpolymers range from about 1.7 to about 3. In another embodiment, the PDI of the terpolymers range from about 1.9 to about 2.5. In another embodiment, the PDI of the terpolymers range from about 2.1 to about 2.3.

The terpolymers of the present invention are useful for the delivery and controlled release of drugs. Drugs that are suitable for release from the terpolymers of the present invention include, but are not limited to, anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

In one embodiment of the present invention the drugs controllably released from the terpolymer include, but are not limited to, macrolide antibiotics including FKBP-12 binding agents. Exemplary drugs of this class include sirolimus (rapamycin) (Formula 2), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent Ser. No. 10/930,487) and zotarolimus (ABT-578; see U.S. Pat. Nos. 6,015,815 and 6,329,386) (Formula 1). Additionally, and other rapamycin hydroxyesters as disclosed in U.S. Pat. No. 5,362,718 may be used in combination with the terpolymers of the present invention. The entire contents of all of preceding patents and patent applications are herein incorporated by reference for all they teach related to FKBP-12 binding compounds and the derivatives.

Formula 1

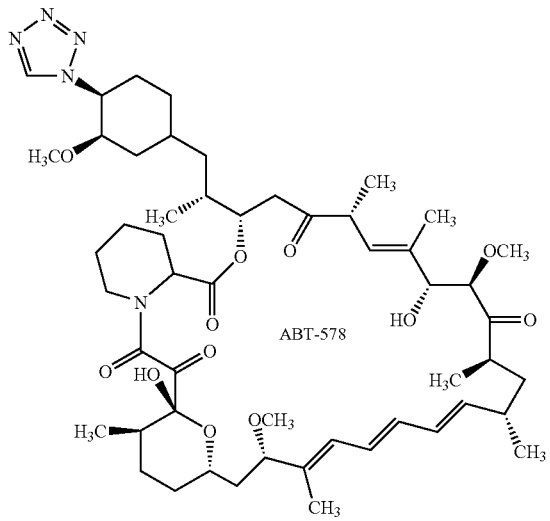

ABT-578

Formula 2

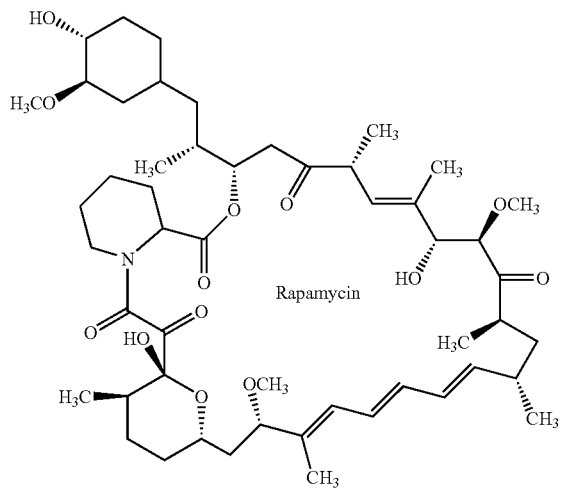

Rapamycin

The controlled release terpolymers of the present invention can be applied to medical device surfaces, either primed or bare, in any manner known to those skilled in the art. Applications methods compatible with the present invention include, but are not limited to, spray coating, electrostatic spray coating, plasma coating, dip coating, spin coating and electrochemical coating.

The terpolymers can be coated on all surfaces of an implantable medical device or only a portion of the medical device such that the medical device contains portions that provide the beneficial effects of the coating and portions that are uncoated. The coating steps can be repeated or the methods combined to provide a plurality of layers of the same coating or a different coating. In one embodiment, each layer of coating comprises a different polymer or the same polymer. In another embodiment each layer comprises the same drug or a different drug.

Furthermore, the gradient polymer-coated medical device can further comprise a top, or cap, coat. A cap coat as used here refers to the outermost coating layer applied over another coating. A drug-releasing gradient polymer coating is optionally applied over the primer coat. A polymer cap coat is applied over the drug-releasing gradient polymer coating. The cap coat may optionally serve as a diffusion barrier to further control the drug release, or provide a separate drug. The cap coat may be merely a biocompatible polymer applied to the surface of the sent to protect the stent and have no effect on elution rates.

Depending upon the type of materials used to form the gradient coatings of the present invention, the coatings can be applied to the surface of a medical device through any of the coating processes known or developed in the art. One method includes directly bonding the gradient coating to the implant's surface. By directly attaching the polymer coating to the implant, covalent chemical bonding techniques are utilized. Generally, the implant surface possesses chemical functional groups on its surface such as carbonyl groups, primary amines, hydroxyl groups, or silane groups which will form strong, chemical bonds with similar groups on the active compounds utilized. In the absence of such chemical forming functional group, known techniques can be utilized to activate the material's surface before coupling the biological compound. Surface activation is a process of generating, or producing, reactive chemical functional groups using chemical or physical techniques such as, but not limited to, ionization, heating, photochemical activation, oxidizing acids, and etching with strong organic solvents.

Alternatively, the gradient coating can be indirectly bound to the implant's surface through an intermediate layer (not shown). This intermediate layer can be either covalently bound to the fixed substrate's surface or bonded through intermolecular attractions such as ionic or Van der Waals forces. Examples of commonly used intermediate layers within the scope of the present invention include, but are not limited to, organic polymers such as silicones, polyamines, polystyrene, polyurethane, acrylates, methoxysilanes, and others.

According to the teachings of the present invention, the implant also can be provided with a non-erodible base coating. The base coating can be provided so as to enhance the biocompatibility of the implant. Exemplary base coatings can be selected from the group consisting of polyurethanes, silicones and polysilanes. Other polymers that can be utilized include polyolefins, polyisobutylene and ethylene-alphaolefin copolymers; acrylic polymers and copolymers, ethylene-co-vinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; and carboxymethyl cellulose. In accordance with the teachings of the present invention, the base coating can also include, without limitation, antibiotics, anti-inflammatory agents, lubricity-enhancing agents, anti-coagulants, anti-metabolites, anti-thrombogenic agents, immunosuppressive agents, muscle relaxants, proteins, peptides, and hormones.

In one embodiment of the present invention, controlled release terpolymers of the present invention are chosen for a particular use based upon its physical properties. For example, a terpolymer coating provides additional structural support to a medical device by increasing the content of butyl methacrylate in the terpolymer. In still another embodiment, a polymer coating on a medical device decreases friction between the medical device and the surrounding tissue, or between the medical device and the delivery system, facilitating the implantation procedure.

EXAMPLES

The following non limiting examples provide methods for the synthesis of exemplary controlled release terpolymers according to the teachings of the present invention.

Example 1

Example 1 is illustrative of the synthesis of a controlled release terpolymer.

To a 500 mL three-neck round bottom glass equipped with a mechanical stirrer is added butyl methacrylate (81 g, 0.57 mol), hexyl methacrylate (9 g, 0.05 mol) and N-vinyl pyrrolidone (10 g, 0.09 mol) in a mixture of n-propyl alcohol and 2-butanone (70:30, 2-butanone:n-propyl alcohol, 200 mL) and 2,2'-azobis(2-methylpropionitrile) (0.8 g, 0.8 wt. %). A net positive pressure of nitrogen is introduced and the reaction heated (60° C.) for 5 hours. Then the reaction is allowed to cool (23° C.). The polymer solution is poured into cold methanol (−60° C.) and a white polymer is precipitated out. All the solvents are decanted and the polymer is re-dissolved in chloroform. This procedure is repeated three times. Then, the polymer is placed in vacuum and the solvent removed in vacuo, yielding the solid polymer.

Example 2

Example 2 is illustrative of the synthesis of a controlled release terpolymer.

To a 500 mL three-neck round bottom glass equipped with a mechanical stirrer is added butyl methacrylate (72 g, 0.51 mol), hexyl methacrylate (18 g, 0.10 mol) and N-vinyl pyrrolidone (10 g, 0.09 mol) in a mixture of n-propyl alcohol and 2-butanone (70:30, 2-butanone:n-propyl alcohol, 200 mL) and 2,2'-azobis(2-methylpropionitrile) (0.8 g, 0.8 wt. %). A net positive pressure of nitrogen is introduced and the reaction heated (60° C.) for 5 hours. Then the reaction is allowed to cool (23° C.). The polymer solution is poured into cold methanol (−60° C.) and a white polymer is precipitated out. All the solvents are decanted and the polymer is re-dissolved in chloroform. This procedure is repeated three times. Then, the polymer is placed in vacuum and the solvent removed in vacuo, yielding the solid polymer.

Example 3

Example 3 is illustrative of the synthesis of a controlled release terpolymer.

To a 500 mL three-neck round bottom glass equipped with a mechanical stirrer is added butyl methacrylate (9 g, 0.06 mol), hexyl methacrylate (81 g, 0.45 mol) and N-vinyl pyrrolidone (10 g, 0.09 mol) in a mixture of n-propyl alcohol and 2-butanone (70:30, 2-butanone:n-propyl alcohol, 200 mL) and 2,2'-azobis(2-methylpropionitrile) (0.8 g, 0.8 wt. %). A net positive pressure of nitrogen is introduced and the reaction heated (60° C.) for 5 hours. Then the reaction is allowed to cool (23° C.). The polymer solution is poured into cold methanol (−60° C.) and a white polymer is precipitated out. All the solvents are decanted and the polymer is re-dissolved in chloroform. This procedure is repeated three times. Then, the polymer is placed in vacuum and the solvent removed in vacuo, yielding the solid polymer.

Example 4

Example 4 describes one non-limiting method for coating a vascular stent with drug containing terpolymers.

To a solution of coating polymer (controlled release terpolymers) and rapamycin in tetrahydrofuran is added a vascular stent. The vascular stent is removed and allowed to dry, the solvent evaporated. A drug eluting stent is presented. The controlled release polymeric coatings of the present invention can be applied to medical device surfaces, either primed or bare, in any manner known to those skilled in the art. Applications methods compatible with the present invention include, but are not limited to, spraying, dipping, brushing, vacuum-deposition, and others. Moreover, the controlled-release coatings of the present invention may be used with a cap coat. A cap coat as used here refers to the outermost coating layer applied over another coating. A drug-releasing copolymer coating is applied over the primer coat. A polymer cap coat is applied over the drug-releasing copolymer coating. The cap coat may optionally serve as a diffusion barrier to further control the drug release, or provide a separate drug. The cap coat may be merely a biocompatible polymer applied to the surface of the sent to protect the stent and have no effect on elution rates. One aspect of the present invention is to provide a biodegradable cap coat that protects the device and bioactive agent from the environment until implanted. After implantation is complete, the biodegradable cap coat degrades at a predetermined rate (made possible by the additional and modification of functional groups to the polymer backbone as made in accordance with the teachings of the present invention) exposing the medical device surface and bioactive agent to the physiological environment.

Example 5

Table 1 contains characterization data on exemplary controlled release terpolymers of the present invention synthesized by the methods of Examples 1-3. Feed composition refers to the amounts of monomers added into the reaction mixture in grams.

TABLE 1

| Polymer | Monomers | Feed Composition | $M_n$ | $M_w$ | PDI | Tg (° C.) |
|---|---|---|---|---|---|---|
| C111 | BMA/HMA/NVP | 81/9/10 | 86408 | 168792 | 1.95 | 32.14 |
| C112 | BMA/HMA/NVP | 72/18/10 | 86977 | 173090 | 2.00 | 28.07 |
| C113 | BMA/HMA/NVP | 63/27/10 | 93210 | 177534 | 1.91 | 24.37 |
| C114 | BMA/HMA/NVP | 54/36/10 | 90775 | 176510 | 1.95 | 20.82 |
| C120 | BMA/HMA/NVP | 45/45/10 | 365437 | 676708 | 1.85 | 13.75 |
| C121 | BMA/HMA/NVP | 36/54/10 | 408068 | 741445 | 1.82 | 11.20 |
| C115 | BMA/HMA/NVP | 27/63/10 | 73579 | 161711 | 2.11 | 8.71 |
| C116 | BMA/HMA/NVP | 18/72/10 | 73289 | 161247 | 2.21 | 2.12 |
| C117 | BMA/HMA/NVP | 9/81/10 | 71709 | 161202 | 2.25 | −2.29 |
| C89 | BMA:HMA:NVP | 47/47/6 | ND | ND | ND | ND |
| C90 | BMA:HMA:NVP | 34/53/13 | ND | ND | ND | ND |

ND = not determined.

Figure 2:
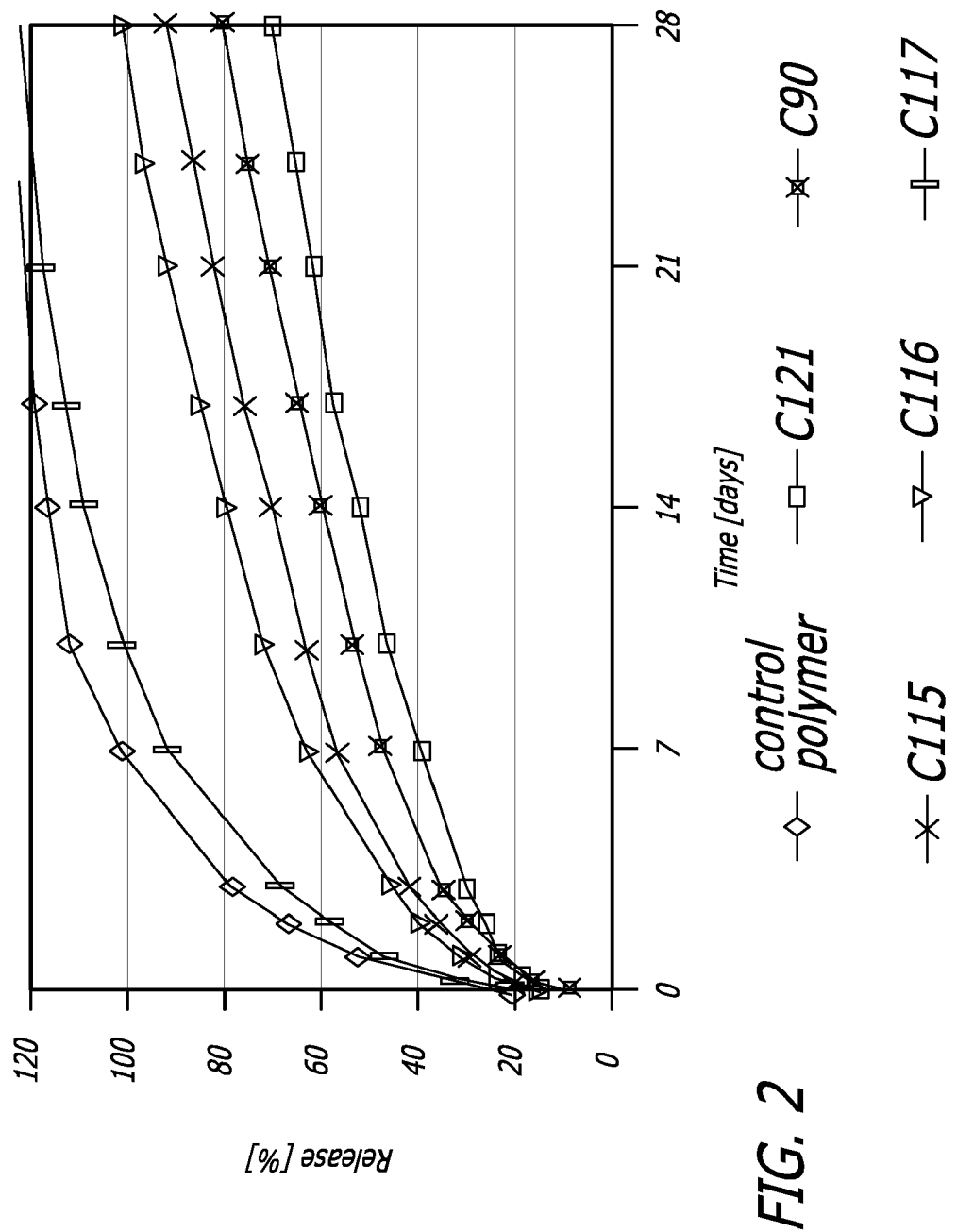
FIG. 2 depicts the drug elution profile of rapamycin from stents coated with terpolymers 6, 11, 7, 8 and 9 (see Table 1) according to the teachings of the present invention.

The drug elution profiles of rapamycin from stents coated with the exemplary terpolymers of the present invention are depicted in FIG. 1 (terpolymers C111, C12, C113, C114, C120 and C89) and FIG. 2 (terpolymers C121, C115, C116, C117 and C90). The control polymer is a blend of three polymers, C10 (BMA:VA at a ratio of 95:5), C19 (HMA:VA:VP at a ratio of 79:5:16) and PVP at a blend ration of 27:63:10 and is disclosed in co-pending U.S. Patent Application Publication No. 2005/0084515 A1 which is incorporated herein in its entirety for all it contains regarding biocompatible controlled release coatings for medical devices.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable medical device comprising a controlled-release terpolymer coating on at least one surface of said medical device and at least one drug, said drug releasable from said terpolymer coating, wherein said controlled release terpolymer comprises the structure of Formula 3,

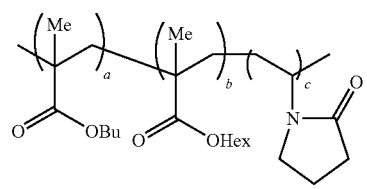

Formula 3

Bu = CH$_2$CH$_2$CH$_2$CH$_3$
Hex = CH$_2$CH$_2$CH$_2$CH$_2$CH$_2$CH$_3$ wherein a is an integer from about 2 to about 30,000, b is an integer from about 2 to about 30,000, and c is an integer from about 2 to about 30,000 and wherein said drug comprises zotarolimus.

* * * * *